US011992327B2

(12) United States Patent
Xu et al.

(10) Patent No.: US 11,992,327 B2
(45) Date of Patent: May 28, 2024

(54) METHODS FOR SWEAT VOLUME DETECTION BASED ON SWEAT PRINT IMAGING (71) Applicant: CHONGQING NORSDA MEDICAL DEVICE CO., LTD., Chongqing (CN)

(72) Inventors: Xiaobo Xu, Chongqing (CN); Ping Wang, Chongqing (CN); Rong Li, Chongqing (CN); Bin Fang, Chongqing (CN); Jiacao Zhou, Chongqing (CN)

(73) Assignee: CHONGQING NORSDA MEDICAL DEVICE CO., LTD., Chongqing (CN)

( * ) Notice: Subject to any disclaimer, the term of this patent is extended or adjusted under 35 U.S.C. 154(b) by 0 days.

(21) Appl. No.: 18/451,822

(22) Filed: Aug. 17, 2023

(65) Prior Publication Data
US 2024/0065611 A1 Feb. 29, 2024

(30) Foreign Application Priority Data
Aug. 18, 2022 (CN) .......................... 202210991410.1

(51) Int. Cl.
*A61B 5/00* (2006.01)
(52) U.S. Cl.
CPC .......... *A61B 5/4266* (2013.01); *A61B 5/0077* (2013.01); *A61B 5/7267* (2013.01)
(58) Field of Classification Search
None
See application file for complete search history.

(56) References Cited

U.S. PATENT DOCUMENTS

2017/0231571 A1\* 8/2017 Rogers ................ A61B 5/4266
600/301
2017/0296114 A1 10/2017 Ghaffari et al.
(Continued)

FOREIGN PATENT DOCUMENTS

CN 112218576 A 1/2021
CN 215375433 U 12/2021
(Continued)

OTHER PUBLICATIONS

First Office Action in Chinese Application No. 202210991410.1 dated Feb. 8, 2023, 12 pages.
(Continued)

*Primary Examiner* — Michael R Bloch
(74) *Attorney, Agent, or Firm* — Porus IP LLC (57) ABSTRACT

The present disclosure provides a method for sweat volume detection based on sweat print imaging, comprising: obtaining a raw data set, the raw data set including at least one sweat print image formed by dropping different volumes of sweat on a test paper under different environmental parameters; obtaining a color value extreme of the sweat print image and dividing the sweat print image into at least one region; calculating a sweat error based on a total sweat collection volume and a real sweat volume; obtaining a trained error prediction model; obtaining a to-be-tested sweat print image and current environmental parameters; inputting the current environmental parameters and a count of regions of the to-be tested sweat print image into the trained error prediction model to determine a sweat error of the to-be-tested sweat print image; calculating a sweat volume and a sweat rate based on the sweat error.

11 Claims, 4 Drawing Sheets (56) References Cited

U.S. PATENT DOCUMENTS

2018/0064377 A1* 3/2018 Rogers .................. B01L 3/5027
2019/0365299 A1  12/2019 Carroll et al.

FOREIGN PATENT DOCUMENTS

| CN | 215837161 U  | 2/2022  |
| EP | 3445230 A1   | 2/2019  |
| JP | S61198039 A  | 9/1986  |
| JP | 2010051347 A | 3/2010  |
| WO | 2020209449 A1| 10/2020 |

OTHER PUBLICATIONS

Decision to Grant a Patent in Chinese Application No. 202210991410.1 dated Feb. 23, 2023, 6 pages.

* cited by examiner

METHODS FOR SWEAT VOLUME DETECTION BASED ON SWEAT PRINT IMAGING

CROSS-REFERENCE TO RELATED APPLICATIONS

This application claims priority of Chinese Patent Application No. 202210991410.1, filed on Aug. 18, 2022, the entire contents of which are incorporated herein by reference.

TECHNICAL FIELD

The present disclosure relates to the field of sweat volume detection, and in particular, to a method for sweat volume detection based on sweat print imaging.

BACKGROUND

Sweating is a form of thermoregulation that relies on sweat evaporation to increase an amount of heat dissipated by a human body. When an environmental temperature rises or the human body is in a high-intensity operation, sweat glands secrete sweat to carry away the body's heat, thus achieving a purpose of maintaining a constant body temperature. The study of human sweat volume and sweat rate effectively determine a sweating physique of the human body, providing guidance on an amount of exercise and a duration of high-intensity work, as well as guidance on drinking water.

Existing manners for sweat volume measurement include a dress weight difference manner, a gauze weight gain manner, a test paper color change manner, etc. The test paper color change manner includes putting a test paper on a to-be-tested part of the human body, the color of the test paper changing after absorbing the sweat, and comparing a color card with the changed color of the test paper to calculate the human body's sweat rate. However, this manner has the following limitations during the detection process: there are variations in sweat production across different parts of the body, and the test paper does not adhere uniformly to every region, resulting in significant differences in the range of color change. Consequently, relying solely on comparing the changed color of the test paper with the color card leads to substantial measurement errors. Additionally, environmental factors such as temperature and humidity affect the color-changing reaction of the test paper, further compromising its accuracy. Therefore, the existing test paper color change manner poses technical challenges in accurate sweat volume detection.

In view of this, the present disclosure wishes to provide a method for sweat volume detection based on sweat print imaging that improves the accuracy of sweat detection.

SUMMARY

One or more embodiments of the present disclosure provide a method for sweat volume detection based on sweat print imaging, the method comprising: data collecting: obtaining a raw data set, the raw data set including at least one sweat print image formed by dropping different volumes of sweat on a test paper under different environmental parameters, the environmental parameters including a temperature and a humidity; image partitioning: identifying a color value of the sweat print image, obtaining a color value extreme, and dividing the sweat print image into a preset count of regions according to the color value extreme; error calculating: calculating a total sweat collection volume of the sweat print image and calculating a sweat error based on the total sweat collection volume and a real sweat volume; model constructing: constructing an error prediction model based on a Back-propagation (BP) neural network using the temperature, the humidity, and a count of regions as an input and the sweat error as an output; model training: using the temperature, the humidity, and the count of regions of the raw data set as the input, training parameters of the error prediction model to obtain a trained error prediction model; sweat volume predicting: pasting a test paper to a to-be-tested part of a tester to obtain a to-be-tested sweat print image formed on the test paper after a preset time period; dividing the to-be-tested sweat print image into at least one region and calculating a total sweat collection volume of the to-be-tested sweat print image; obtaining current environmental parameters, inputting the current environmental parameters and a count of regions of the to-be-tested sweat print image into the trained error prediction model, and determining a sweat error of the to-be-tested sweat print image; calculating a sweat volume and a sweat rate of the to-be-tested part based on the sweat error of the to-be-tested sweat print image, wherein the sweat error is obtained by: obtaining a sweat collection volume of the at least one region and summing the sweat collection volume of the at least one region to obtain the total sweat collection volume: $Q'_i = (kx'_1+b)a_1 + (kx'_2+b)a_2 + , \ldots, (kx'_p+b)a_p, \ldots, +(kx'_m+b)a_m$, herein $x'_p$ denotes a median color value of a p-th region, $a_p$ denotes an area of the p-th region, k and b both denote preset coefficients, $(ky'_p+)a_p$ denotes a sweat collection volume of the p-th region, $Q'_i$ denotes the total sweat collection volume, and m denotes the count of regions; and determining the sweat error based on a difference between the total sweat collection volume and the real sweat volume.

Some embodiments of the present disclosure include at least one following beneficial effect: (1) by detecting the sweat volume of the tester, it is possible to judge a sweating physique and the strength of perspiration function of the tester and to provide guidance for the tester's daily exercise, work intensity, and water supplementation; (2) by collecting and recognizing the sweat print image of a test part of the tester, it can initially calculate a sweat volume of the test part, i.e., the total sweat collection volume, and through the trained error prediction model, the sweat error can be predicted through the error prediction model and an accurate sweat volume can be determined by summing the total sweat collection volume and the sweat error, realizing an accurate and rapid detection of the sweat volume; and (3) when calculating the total sweat collection volume, a count of segments of color value is determined based on the color value extreme, when the color value extreme is small, the amount of calculation during the detection process is reduced by decreasing the count of segments, and when the color value extreme is large, the calculation accuracy is ensured by increasing the count of segments.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering indicates the same structure, wherein.

DETAILED DESCRIPTION

In order to more clearly illustrate the technical solutions of the embodiments of the present disclosure, the accompanying drawings to be used in the description of the embodiments will be briefly described below. It will be apparent that the accompanying drawings in the following description are only some examples or embodiments of the present disclosure, and that the present disclosure can be applied to other similar scenarios in accordance with these drawings without creative labor for those of ordinary skill in the art. Unless obviously obtained from the context or the context illustrates otherwise, the same numeral in the drawings refers to the same structure or operation.

Unless the context clearly suggests an exception, the words "one," "a," "an," and/or "the" do not refer specifically to the singular. The words "one", "a", "an" and/or "the" do not refer to the singular, but may include the plural as well. In general, the terms "including" and "comprising" suggest only the inclusion of clearly identified steps and elements, which do not constitute an exclusive list, and the method or apparatus may also include other steps or elements.

Flowcharts are used in the present disclosure to illustrate operations performed by a system according to embodiments of the present disclosure. It should be understood that the preceding or following operations are not necessarily performed in an exact sequence. Instead, the steps can be processed in reverse order or simultaneously. It is also possible to add other operations to these processes, or to remove a step or steps from them.

An existing method for sweat volume measurement has the following limitations during the detection process: there are variations in sweat production across different parts of the body, and the test paper does not adhere uniformly to every region, resulting in significant differences in the range of color change. Consequently, relying solely on comparing the changed color of the test paper with the color card leads to substantial measurement errors. Additionally, environmental factors such as temperature and humidity affect the color-changing reaction of the test paper, further compromising its accuracy. Therefore, the existing test paper color change manner poses technical challenges in accurate sweat volume detection. In view of this, the present disclosure provides a method for sweat volume detection based on sweat print imaging, which can realize an accurate and rapid detection of sweat volume.

Figure 1:
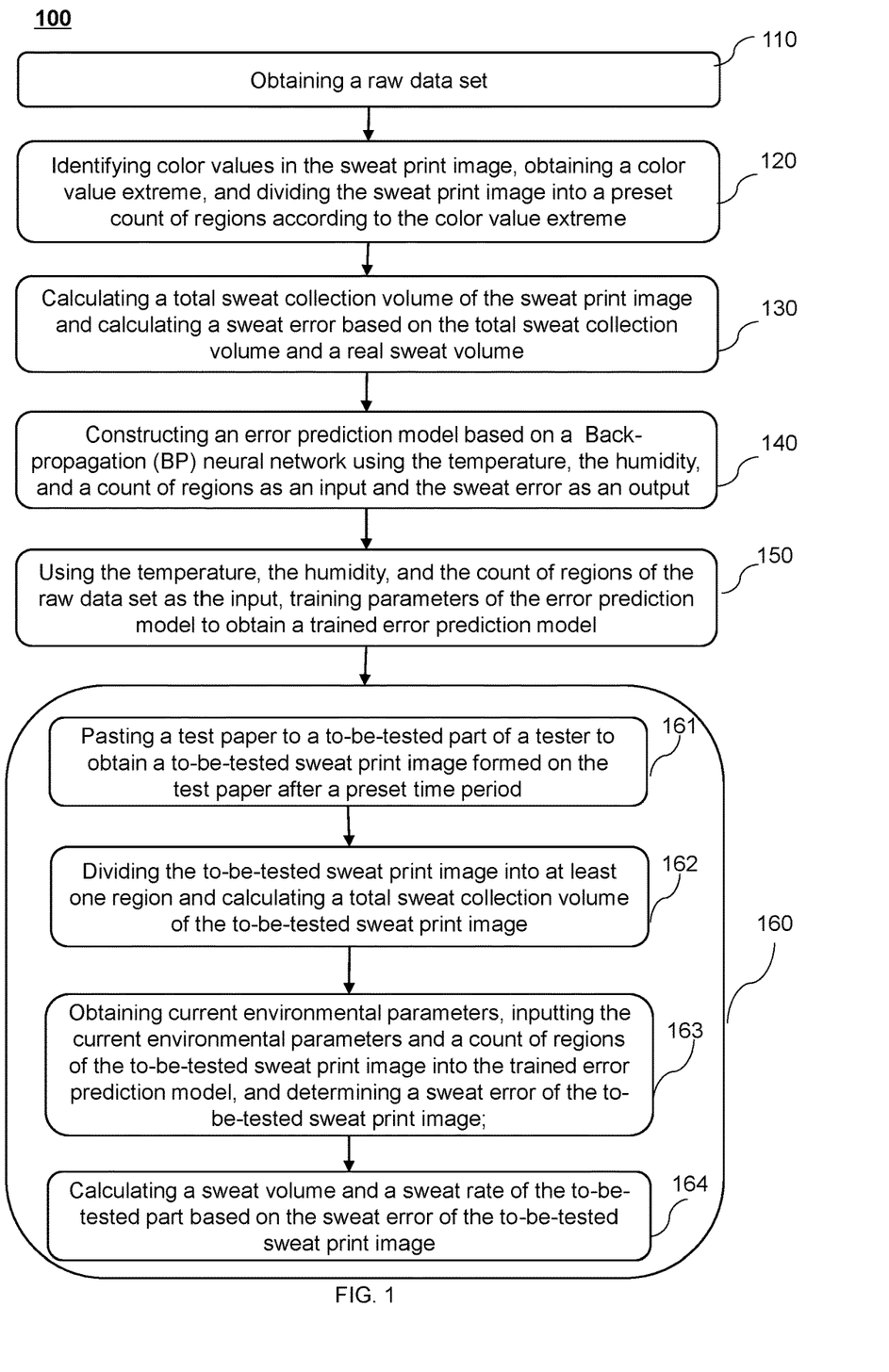
FIG. 1 is a flowchart illustrating an exemplary method for sweat volume detection based on sweat print imaging according to some embodiments of the present disclosure.

FIG. 1 is a flowchart illustrating an exemplary method for sweat volume detection based on sweat print imaging according to some embodiments of the present disclosure. In some embodiments, a process 100 may be performed based on a system for sweat detection.

In some embodiments, the system for sweat detection includes at least one processor and at least one memory; the at least one memory is used to store computer instructions; and the at least one processor is used to execute at least a part of the computer instructions to implement the method for sweat volume detection based on sweat print imaging.

As shown in FIG. 1, the process 100 includes following steps.

In some embodiments, the processor may collect data through step 110. Step 110 includes: obtaining a raw data set.

The raw data set is a collection of samples used to train an initial error prediction model to obtain a sweat error.

In some embodiments, the raw data set includes at least one sweat print image formed by dropping different volumes of sweat on a test paper under different environmental parameters.

The test paper is a chemical test strip used to detect a sweat volume. The color of the test paper changes as absorbing sweat. Different sweat volumes make the test paper appear different colors.

The environmental parameters are parameters related to a collection environment. The collection environment is an environment in which the raw data set is collected.

In some embodiments, the environmental parameters include a temperature and a humidity.

The environmental parameters may be obtained in various ways. In some embodiments, the environmental parameters may be obtained by a sensor displaced within the collection environment. Exemplarily, the sensor may include a temperature sensor, a humidity sensor, or the like. For example, the temperature of the collection environment may be obtained by the temperature sensor, and the humidity of the collection environment may be obtained by the humidity sensor.

In some embodiments, the environmental parameters also include a wind speed. Accordingly, the sensor may also include an airflow sensor, and the wind speed may be obtained by the airflow sensor.

The wind speed affects sweat evaporation, and the sweat print image may be affected by different wind speeds. In some embodiments of the present disclosure, obtaining the wind speed by means of the airflow sensor can improve the reliability of the subsequent calculation of a total sweat collection volume and improve the accuracy of data.

The sweat print image may be an image formed by sweat on the test paper. In some embodiments, the sweat print image may be collected based on an imaging camera taking a picture of a test paper dropping with sweat.

The raw data set may be obtained in a variety of ways. For example, the raw data set may be obtained based on a large number of experiments and stored in a storage device, and the processor may access the raw data set when it communicates with the storage device.

In some embodiments, different volumes of sweat may be dropped on the test paper under different temperatures and humidities, and the sweat print image formed by the sweat on the test paper may be collected. For example, it is possible to drop different volumes of sweat on a test paper at a certain value of temperature and a certain value of humidity in an environment, and a sweat print image formed by the sweat on the test paper may be collected.

In some embodiments, different volumes of sweat may be dropped on the test paper at different temperatures, different humidities, and different wind speeds, and a sweat print image formed by the sweat on the test paper may be collected. For example, it is possible to drop different volumes of sweat on a test paper at a certain value of temperature, a certain value of humidity, and a certain value of wind speed in an environment, and a sweat print image formed by the sweat on the test paper may be collected.

In some embodiments, the data collecting is implemented by setting at least one set of experimental environmental parameters, and dropping different volumes of sweat on different test papers under each set of experimental environmental parameters; collecting sweat print images on different test papers to obtain the raw data set; wherein the test papers show different colors according to the different volumes, and the different colors correspond to different color values, and the raw data set is as follows:

$$S=\{s_1(T_1,H_1,Q_1,X_1),s_2(T_2,H_2,Q_2,X_2),\ldots,s_i(T_i,H_i,Q_i,X_i),\ldots,s_n(T_n,H_n,Q_n,X_n)\}$$

where S denotes the raw data set, $s_i$ denotes raw data collected for the i-th time, n denotes a maximum count of sampling times, $T_i$ denotes a temperature collected for the i-th time, $H_i$ denotes a humidity collected for the i-th time, $Q_i$ denotes a real sweat volume collected for the i-th time, and $X_i$ denotes a sweat print image collected for the i-th time.

The experimental environment parameters are environmental parameters in which a data collecting experiment is performed. In some embodiments, the experimental environment parameters may include the temperature, the humidity, or the like. Different sets of experimental environmental parameters may have different temperatures and/or different humidities.

In some embodiments, the experimental environment parameters may also include the wind speed.

In some embodiments of the present disclosure, obtaining a large number of sample sets for training through a plurality of sets of experiments can improve the accuracy and qualification of the sample sets, which is conducive to the subsequent training of the error prediction model.

In some embodiments, the processor may perform image partitioning according to step 120. Step 120 includes: identifying color values in the sweat print image, obtaining a color value extreme, and dividing the sweat print image into a preset count of regions according to the color value extreme.

The color value may be a color value of each pixel point in the sweat print image in a certain color mode. The color mode includes but is not limited to RGB mode and CMYK mode. For example, a color value corresponding to red in the RGB mode is (255, 0, 0), and a color value corresponding to red in the CMYK mode is (C0, M100, Y100, K10).

In some embodiments, the processor may analyze and process the sweat print image through existing software to identify the color value of the each pixel point in the sweat print image. In some embodiments, the processor may analyze and process the sweat print image through a color recognition model to identify the color value of the each pixel point in the sweat print image. The color recognition model may be a pre-trained machine learning model.

The color value extreme may be a difference between a maximum color value and a minimum color value. The maximum color value is a largest color value among the color values of pixel points in the sweat print image. The minimum color value is a smallest color value among the color values of the pixel points in the sweat print image.

In some embodiments, the processor may determine a maximum extreme value and a minimum extreme value of the color value, and calculate the color value extreme based on the maximum extreme value and the minimum extreme value.

The processor may perform the image partitioning in various ways. In some embodiments, the processor may divide the sweat print image into at least one region based on the color values. In some embodiments, the processor may classify a plurality of pixel points with a same color value into a same region. In some embodiments, the processor may preset a plurality of color value ranges based on a priori knowledge or historical data to classify a plurality of pixel points in a same color value range as a same region.

The preset count (i.e., a count of regions) is a count of regions obtained by performing the image partitioning on the sweat print image.

The count of regions may be determined in various ways. In some embodiments, the count of regions may be determined based on an image partitioning result. For example, when classifying a plurality of pixel points with a same color value into a same region, the count of regions may be determined based on a count of color values included in the sweat print image. As another example, when classifying a plurality of pixel points in a same color value range into a same region, the count of regions may be determined based on a count of color value ranges included in the sweat print image.

In some embodiments, the count of regions is determined by a following formula:

$$m_i = \begin{cases} m_1 & \Delta x_i < x_1 \\ m_2 & x_1 < \Delta x_i < x_2 \\ m_3 & x_2 < \Delta x_i < x_3 \\ m_4 & x_3 < \Delta x_i < x_4 \\ m_5 & x_4 < \Delta x_i \end{cases}$$

wherein $m_i$ denotes the count of regions, $x_1$, $x_2$, $x_3$, and $x_4$ denote color value extreme thresholds, $\Delta x_i$ denotes the color value extreme, and $m_1$, $m_2$, $m_3$, $m_4$ and $m_5$ denote a count of regions corresponding to 5 color value extreme ranges respectively.

In some embodiments, the count of regions of the sweat print image may be determined based on a color value extreme range in which the color value extreme of the sweat print image is located. In some embodiments, the processor may preset a corresponding relationship between different color value extreme ranges and different counts of regions based on historical trials or historical data; and obtain the count of regions corresponding to the color value extreme range through querying a table based on the color value extreme range in which the color value extreme is located.

In some embodiments, the color value extreme range may be determined based on the color value extreme threshold. In some embodiments, the color value extreme range may be a range between two adjacent color value extreme thresholds. For example, if the color value extreme threshold is $x_1$, $x_2$, $x_3$, and $x_4$, the color value extreme range includes ($\Delta x_i < x_1$), ($x_1 < \Delta x_i < x_2$), ($x_2 < \Delta x_i < x_3$), ($x_3 < \Delta x_i < x_4$) and ($x_4 < \Delta x_i$), wherein ($\Delta x_i < x_1$) denotes that the color value extreme range is a range between a minimum color value extreme threshold (e.g., 0) and $x_1$, and ($x_4 < \Delta x_i$) denotes that the color value extreme range is a range between a maximum color value extreme threshold (e.g., a value of the maximum color value range) and $x_4$.

The color value extreme threshold may be determined in various ways. In some embodiments, the color value extreme threshold may be a system default value, an empirical value, a human pre-set value, or the like, or any combination thereof, and may be set according to an actual need, and the present disclosure does not limit herein. In some embodiments, the color value extreme threshold may be determined based on a color value critical point at which the test paper occurs a color change. For example, a difference between two adjacent color value critical points at which a color change occurs may be determined as the color value extreme threshold. For example, if a color value of 10 is a critical point at which the test paper changes from dark blue to light blue, and a color value of 40 is a critical point at which the light blue changes to light pink, then 30 may be used as the color value extreme threshold.

In some embodiments, a plurality of color value extreme thresholds and a count of the plurality of color value extreme thresholds in a color value range of the test paper may be determined based on a plurality of color development experiments of the test paper by experimenters. In some embodiments, a color development pattern of the test paper may also be obtained from manufacturers of the test paper, which in turn determines the plurality of color value extreme thresholds and the count of the plurality of color value extreme thresholds in a color value range of the test paper.

In some embodiments of the present disclosure, a reasonable count of regions may be obtained relatively quickly by determining the count of regions based on the color value extreme range at which the color value extreme locates.

In some embodiments, the sweat print image may also be divided into a preset count of regions by a preset division algorithm. More on this embodiment can be found in the relevant description of FIG. 2.

In some embodiments, error calculating may be performed by step 130. Step 130 includes: calculating a total sweat collection volume of the sweat print image and calculating a sweat error based on the total sweat collection volume and a real sweat volume.

The total sweat collection volume may be a total value of a volume of sweat collected on the test paper.

In some embodiments, the processor may sum sweat collection volumes of each region to obtain the total sweat collection volume of the sweat print image. The sweat collection volume of the each region may be determined based on a mean color value or a median color value of the each region. For example, the processor may determine the mean color value or median color value of each region, and based on a corresponding relationship between the color value and a sweat volume, determine a sweat collection volume corresponding to the mean color value or the median color value of each region. In some embodiments, the processor may obtain a sweat collection volume of the at least one region and sum the sweat collection volume of the at least one region to obtain the total sweat collection volume:

$$Q' = (kx'_1+b)a_1 + (kx'_2+b)a_2 + ,\ldots, (kx'_p+b)a_p, \ldots, +(kx'_m+b)a_m$$

where $x'_p$ denotes a median color value of a p-th region, $a_p$ denotes an area of p-th region, k and b both denote preset coefficients, $(ky'_p+b)a_p$ denotes a sweat collection volume of p-th region, $Q'_i$ denotes the total sweat collection volume, and m denotes the count of regions.

In the above embodiment, each region has a same set of preset coefficients.

The real sweat volume may be an actual volume of the sweat dropped into the test paper. The real sweat volume may be obtained by measuring the sweat before dropping it into the test paper.

The sweat error may be used to represent a deviation between the total sweat collection volume and the real sweat volume.

In some embodiments, the processor may determine the sweat error based on a difference between the total sweat collection volume and the real sweat volume.

The set of preset coefficients corresponding to different regions may be different. In some embodiments, each region corresponds to a set of preset coefficients. Accordingly, the total sweat collection volume may be obtained by a following formula based on the sweat collection volume of the at least one region:

$$Q'_i = (k_1x'_1+b)a_1 + (k_2x'_2+b)a_2 + ,\ldots, (k_px'_p+b_p)a_p, \ldots, +(k_mx'_m+b_m)a_m$$

where $k_p$ and $b_p$ denote preset coefficients of the p-th region. Please refer to above for meanings of other symbols.

In some embodiments, the preset coefficients of the each region are determined based on a color value distribution feature of the each region.

The color value distribution feature may be a feature related to the color values of different pixel points in the sweat print image.

In some embodiments, the color value distribution feature may include a color value histogram distribution and a color value dispersion degree of each pixel point within the region.

The color value histogram distribution may be a proportion distribution of a plurality of pixel points corresponding to the color value range or each color value in the region and all pixel points in the region. For example, the color value histogram distribution is shown in a following table:

| Color value or color value range | A1 | ... |
| Proportion of the pixel points corresponding to the color value in the region | B1 | ... |

For example, if a region covers 10 pixel points, and there are 6 pixel points with a color value of A1, 2 pixel points with a color value of A2, and 2 pixel points with a color value of A3, then the color value histogram distribution of the region is as follows: the proportion of the pixel points corresponding to the color value 1 is 60%, the proportion of the pixel points corresponding to the color value 2 is 20%, and the proportion of the pixel points corresponding to the color value 3 is 20%.

In some embodiments, the processor may determine the color value histogram distribution by calculating a ratio of a count of pixel points with a same color value in the region to a count of total pixel points in the region.

The color value dispersion degree may be a degree of difference in the color values of the pixel points in the region.

In some embodiments, the color value dispersion degree may be determined based on a variance or standard deviation of the color values of the pixel points in the region.

In some embodiments, the processor may preset a corresponding relationship between different color value histogram distributions and preset coefficients and a corresponding relationship between color value dispersion degrees and preset coefficients based on historical experiments or historical data, and determine preset coefficients of a certain region based on a color value distribution feature and the corresponding relationship of the region.

In some embodiments of the present disclosure, by considering a distribution of color values in the region and the color value dispersion degree, the effect of uneven distribution of the color values and excessive deviation of the color values on the region's sweat collection volume can be avoided, and the accuracy of the subsequent calculation of the total sweat collection volume can be improved.

In some embodiments, the preset coefficients of each region are also correlated to a pore density of a skin region in which the each region is located.

The pore density is a distribution density of pores within the skin region. For example, the pore density may be $p_1$ per square centimeter.

In some embodiments, a count of pores and/or a count of sweat hairs in each region may be obtained by taking an image of a skin region corresponding to each region through image recognition, and the pore density may be determined by a preset rule based on the count of pores and/or the count of sweat hairs. For example, a ratio of an average of the count of pores and the count of sweat hairs to an area of the skin region may be determined as the pore density.

In some embodiments, the processor may preset the corresponding relationship between different color value histogram distributions and preset coefficients, the corresponding relationship between color value dispersion degrees and preset coefficients, and a corresponding relationship between different pore densities and preset coefficients based on historical experiments or historical data, and determine preset coefficients of a certain region based on color value distribution feature, an actual pore density, and the corresponding relationship of the region.

In some embodiments of the present disclosure, skin regions with different pore densities have different sweating features, and determining the preset coefficients by taking into account the pore densities of the skin regions can further improve the accuracy of the subsequent calculation of the total sweat collection volume.

In some embodiments, a model may be constructed by step 140. Step 140 includes: constructing an error prediction model based on a Back-propagation (BP) neural network using the temperature, the humidity, and a count of regions as an input and the sweat error as an output.

The error prediction model may be used to obtain the sweat error of the sweat print image.

In some embodiments, the error prediction model may be a machine learning model, e.g., including any one or combination of back-propagation (BP) neural networks or other customized model structures.

In some embodiments, an input of the error prediction model includes the temperature and humidity at the time the sweat print image is collected and the count of regions of the sweat print image, and the output is the sweat error of the sweat print image.

In some embodiments, the BP neural network may include 1 input layer, 2 hidden layers, and 1 output layer. More on a structure of the model can be found in the relevant description of FIG. 3.

In some embodiments, a model training may be performed by step 150. Step 150 includes: using the temperature, the humidity, and the count of regions of the raw data set as the input, training parameters of the error prediction model to obtain a trained error prediction model.

In some embodiments, the error prediction model may be obtained by training based on a plurality of training samples with a label. In some embodiments, the training may be performed by various manners based on the training sample. For example, the training may be performed based on a gradient descent algorithm.

In some embodiments, each set of training samples may include a sample temperature, a sample humidity, and a sample count of regions corresponding to a sample sweat print image, and the training samples may be obtained from historical data.

In some embodiments, the label is a real sweat error of the sample sweat print image corresponding to the training sample. The label may be determined by human labeling. For example, during an experiment, a difference between a real sweat volume and a total sweat collection volume of the sample sweat print image is determined as the label.

Figure 3:
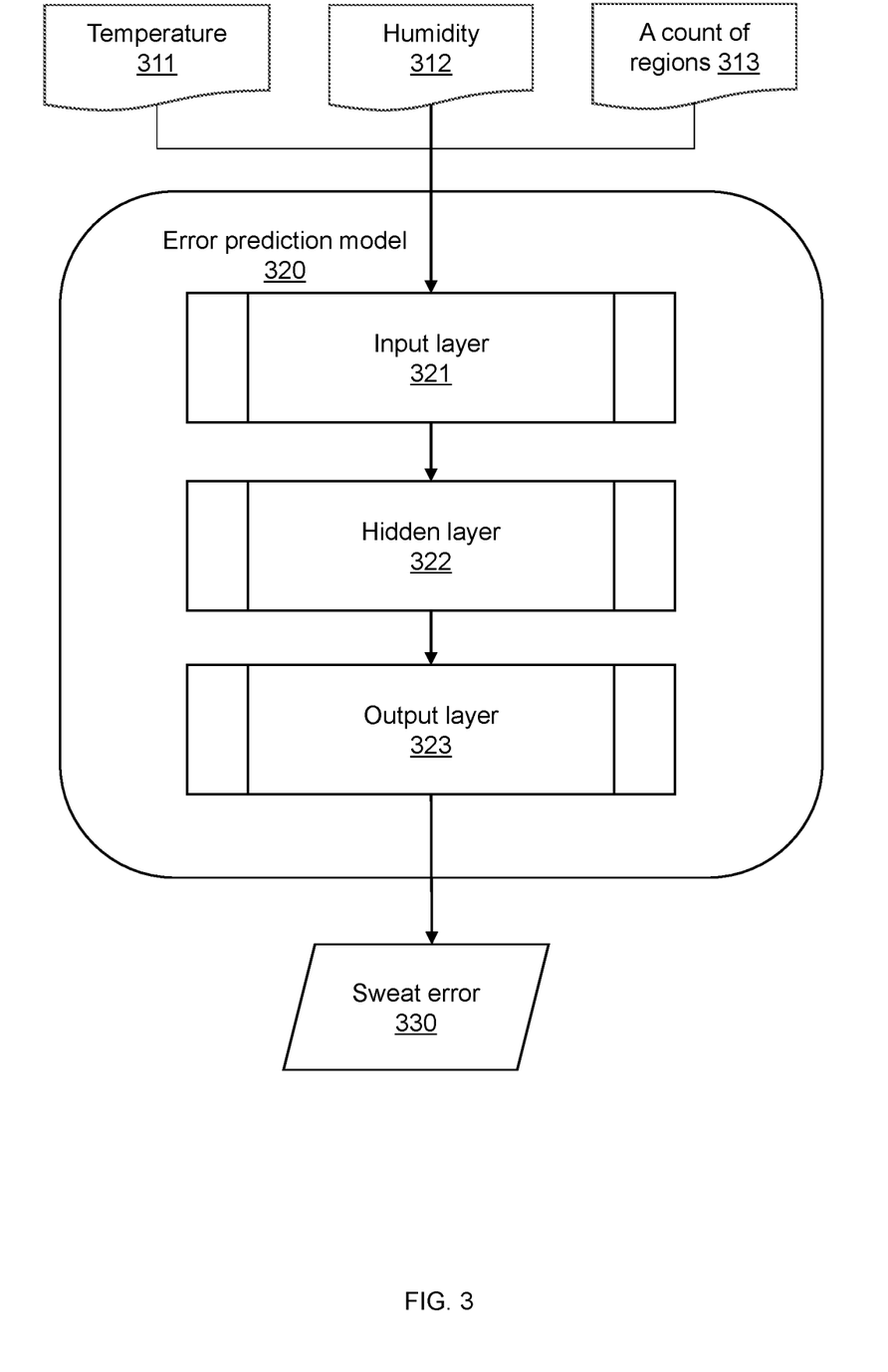
FIG. 3 is a schematic diagram illustrating an exemplary application of an error prediction model according to some embodiments of the present disclosure.

More details about the model training can be found in the related description in FIG. 3.

In some embodiments, sweat predicting may be performed by step 160. Step 160 includes following steps 161 to steps 164 described below.

Step 161, pasting a test paper to a to-be-tested part of a tester to obtain a to-be-tested sweat print image formed on the test paper after a preset time period.

Step 162, dividing the to-be-tested sweat print image into at least one region and calculating a total sweat collection volume of the to-be-tested sweat print image.

Step 163, obtaining the current environmental parameters, inputting the current environmental parameters and a count of regions of the to-be-tested sweat print image into the trained error prediction model, and determining a sweat error of the to-be-tested sweat print image.

Step 164, calculating a sweat volume and a sweat rate of the to-be-tested part based on the sweat error of the to-be-tested sweat print image.

In an actual process for sweat predicting, the test paper may be utilized to collect a sweat volume from the to-be-tested part of the tester, and an image collected after the preset time period is determined as the to-be-tested sweat print image. The to-be-tested part may be set according to an actual need. The preset time period may be determined based on a time when the test paper occurs color development. For example, the preset time period may be a period of time between when the sweat begins to drop into the test paper and when the test paper fully develops color.

The image partitioning and total sweat collection volume calculation for the to-be-tested sweat print image is performed in the same way as the image partitioning and total sweat collection volume calculation for the raw data set, and more details can be found in the previous relevant descriptions, which will not be repeated herein.

The current environmental parameters are environmental parameters that existed at a time the sweat is collected from the to-be-tested part of the tester. In some embodiments, the current environmental parameters may include a temperature and a humidity. In some embodiments, the current environmental parameters may also include a wind speed. The current environment parameters are collected in the same way as the experimental environment parameters, and more details can be found in the previous description, which will not be repeated herein.

In an actual process for sweat predicting, the current environmental parameters and the count of regions of the to-be-tested sweat print image may be input into the trained error prediction model to determine the sweat error of the to-be-tested sweat print image.

In some embodiments, the sweat volume and sweat rate of the to-be-tested part may be obtained in a variety of ways. For example, the sweat volume and sweat rate of the to-be-tested part may be obtained by a wearable sensor displaced at the to-be-tested part.

In some embodiments, the processor may sum the total sweat collection volume of the to-be-tested sweat print image and the sweat error of the to-be-tested sweat print image to obtain the sweat volume of the to-be-tested part.

In some embodiments, the processor may calculate the sweat rate of the to-be-tested part of the tester based on the total sweat collection volume of the to-be-tested sweat print image and the sweat error of the to-be-tested sweat print image. Exemplarily, the sweat rate may be determined by a following formula:

$$R = \frac{Q' + \Delta Q'}{a}$$

where R denotes the sweat rate, a denotes an effective area of the test paper pasted to the to-be-tested part of the tester, Q' denotes the total sweat collection volume of the to-be-tested sweat print image, and ΔQ' denotes the sweat error of the to-be-tested sweat print image.

In some embodiments of the present disclosure, by using the trained error prediction model, the current environmental parameters of the to-be-tested sweat print image and the count of regions can be quickly analyzed to determine the sweat error of the to-be-tested sweat print image, which in turn improves the reliability of calculating the sweat volume and sweat rate.

In some embodiments of the present disclosure, by dropping different volumes of sweat into the test paper under different environmental parameters and collecting corresponding sweat print images as the raw data set, sample diversification can be realized, the accuracy of the trained error prediction model can be improved, and overfitting or underfitting of the error prediction model can be avoided. Based on the trained error prediction model, the sweat error can be obtained efficiently and accurately, which facilitates the efficiency and accuracy of the subsequent calculation of the sweat volume and sweat rate.

Figure 2:
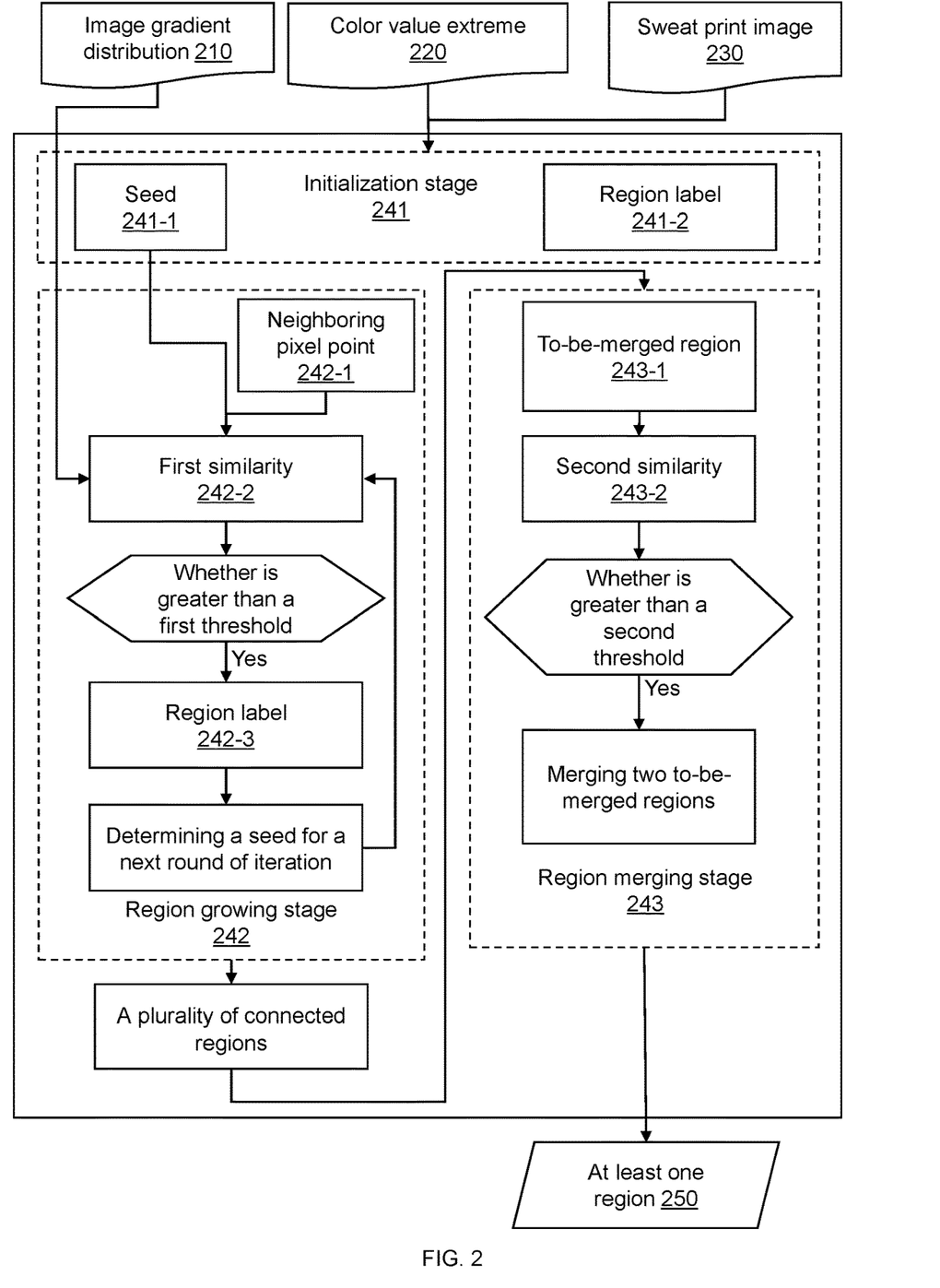
FIG. 2 is a schematic diagram illustrating exemplary image partitioning according to some embodiments of the present disclosure.

FIG. 2 is a schematic diagram illustrating exemplary image partitioning according to some embodiments of the present disclosure.

In some embodiments, the image partitioning may also be performed by: calculating an image gradient distribution 210 of a sweat print image 230; based on a color value extreme 220 and the image gradient distribution 210 of the sweat print image 230, dividing the sweat print image 230 into at least one region 250 using a preset division algorithm 240.

In some embodiments, the image gradient distribution 210 includes an image gradient of each pixel point in the sweat print image.

In some embodiments, for each pixel point, an image gradient of the sweat print image at that pixel point may be determined based on a color value of the pixel point and a color value of a neighboring pixel point. The neighboring pixel point is a pixel point that is in a neighboring region of a certain pixel point. The neighboring region may include 4-neighboring region, 8-neighboring region, diagonal neighboring region, etc. Accordingly, the neighboring pixel point includes a pixel point in the 4-neighboring region, the 8-neighboring region, or the diagonal neighboring region of a certain pixel point. For example, the coordinate of a pixel point P are (x, y), and coordinates of four pixel points in the 4-neighboring region of the pixel point P are (x+1, y), (x−1, y), (x, y+1), and (x, y−1).

In some embodiments, for each pixel point, the image gradient of the sweat print image at the pixel point may be determined based on a color value difference between that pixel point and the neighboring pixel point. For example, the neighboring pixel points of pixel point A include $A_1$ to $A_w$, and the image gradient of the pixel point A may be calculated by a following formula:

$$P_A = \frac{1}{w} \sum_{i}^{w} x(A, A_i)$$

where $P_A$ denotes an image gradient of the pixel point A and $x(A, A_i)$ denotes a color value difference between the pixel point A and the neighboring pixel point $A_i$. $x(A, A_i)$ may be obtained by calculating an absolute value of the color value difference between the pixel point A and the neighboring pixel point $A_i$, and w denotes a count of neighboring pixel points.

The preset division algorithm 240 is an algorithm that performs an image division on the sweat print image to obtain at least one region. For example, the preset division algorithm 240 may include, but is not limited to, a combination of one or more of a threshold algorithm, a region growing algorithm, an edge detection algorithm, or the like.

In some embodiments, referring to FIG. 2, the preset division algorithm 240 may include an initialization stage 241, a region growing stage 242, and a region merging stage 243.

In some embodiments, the processor may process the initialization stage 241, the region growing stage 242, and the region merging stage 243 respectively based on the color value extreme 220 and the image gradient distribution 210 of the sweat print image 230 to divide the sweat print image 230 into the at least one region 250.

In some embodiments, the initialization stage 241 includes: determining a preset count of pixel points in the sweat print image 230 as seeds 241-1 based on the color value extreme 220, and assigning a region label 241-2 for each seed 241-1.

In some embodiments, the preset count may be positively correlated with the color value extreme 220, and the greater the color value extreme 220, the greater the preset count.

In some embodiments, the preset count is greater than or equal to a count threshold. It should be noted that the preset count needs to satisfy that a count of regions after the image partitioning is not less than the count threshold. The count threshold may be set based on empirical or experiment.

The region label may be used to reflect a region to which the pixel point belongs. For example, pixel points labeled with a same region label belong to a same region.

In some embodiments, the processor may select a preset count of pixel points as the seeds 241-1 based on a first preset constraint and a second preset constraint. For example, the processor may randomly select a preset count of pixel points as the seeds 241-1 among pixel points that satisfy both the first preset constraint and the second preset constraint.

The first preset constraint may be a judgment condition for evaluating a distance between the seeds 241-1. In some embodiments, the first preset constraint may be that the distance between any two seeds 241-1 is not less than a preset distance threshold.

In some embodiments, the preset distance threshold is negatively correlated with the color value extreme 220, and the greater the color value extreme 220, the smaller the preset distance threshold.

The second preset constraint may be a judgment condition for assessing whether color values of the seeds 241-1 are uniformly distributed. In some embodiments, color values of pixel points in the sweat print image may be divided into a plurality of color value intervals based on a bucket principle. Accordingly, the second preset constraint may be: ensuring that at least one seed 241-1 exists in each color value interval, i.e., the color value of the seed 241-1 falls within that color value interval. A count of color value intervals and a width of the color value interval may be determined based on a priori knowledge.

Seeds selected through the above manner can be dispersed as much as possible to facilitate the performance on the region growing stage.

In some embodiments, the region growing stage 242 includes: performing a plurality of rounds of iterations. At least one round of iteration includes: determining one or more seeds 241-1 of a current round of iteration; for each of the one or more seeds 241-1 of the current round of iteration, calculating a first similarity 242-2 between the seed 241-1 and a neighboring pixel point 242-1 of the seed 241-1; assigning a neighboring pixel point whose first similarity 242-2 with the seed 241-1 is greater than the first threshold with the region label 242-3 corresponding to the seed 241-1, and determining the neighboring pixel point as a seed for a next round of iteration.

The first similarity 242-2 may be a similarity between two pixel points. For example, the first similarity 242-2 may include a similarity between the seed 241-1 and the neighboring pixel point 242-1 of the seed 241-1. See the previous section for a more detailed description of the neighboring pixel point.

In some embodiments, the first similarity 242-2 may be determined based on a color value difference and an image gradient difference between the seed 241-1 and the neighboring pixel point 242-1 of the seed 241-1. An exemplary manner of calculation is as follows:

$$Z = \frac{r1}{r2 \times \Delta c1 + r3 \times \Delta c2}$$

where z denotes the first similarity between the seed 241-1 and the neighboring pixel point 242-1 of the seed 241-1, $\Delta c1$ denotes the color value difference between the seed 241-1 and the neighboring pixel point 242-1 of the seed 241-1, and $\Delta c2$ denotes the image gradient difference between the seed 241-1 and the neighboring pixel point 242-1 of the seed 241-1, r1, r2, and r3 denote preset coefficients, and r1, r2, and r3 may be obtained based on system defaults or human presets.

A first threshold is a threshold condition related to the first similarity 242-2. The first threshold may be obtained by the system or by a human preset.

In some embodiments, the processor may perform different rounds of iterations for the seeds 241-1 with different region labels 242-3. For a seed 241-1 with a certain region label, in each of a plurality of rounds of iterations which it corresponds to, it may be determined whether the neighboring pixel point 242-1 (which has not been labeled with a region label) of the seed 241-1 may be labeled with the region label 242-3 corresponding to the seed 241-1. When the first similarity 242-2 between the neighboring pixel point 242-1 and the seed 241-1 is greater than the first threshold, the neighboring pixel point 242-1 may be labeled with the region label 242-3 corresponding to the seed 241-1. A round of iteration is completed after judging whether all neighboring pixel points 242-1 of the seed 241-has been labeled with the region label 242-3 corresponding to the seed 241-1.

In some embodiments, the processor may determine the neighboring pixel point 242-1 whose first similarity 242-2 with the seed 241-1 in a current round of iteration is greater than the first threshold as a seed for a next round of iteration, and determine whether a neighboring pixel point of the seed for the next round of iteration is capable of being labeled with a region label corresponding to the seed. The above steps are repeated to determine whether region labeling need to be performed until the iteration is ended when a first iteration condition is satisfied, and a connected region with a certain region label is obtained. A plurality of pixel points with a same region label may form the connected region.

For seeds with different region labels, a plurality of rounds of iterations as described above can eventually lead to a plurality of connected regions of the sweat print image.

The first iteration condition is a judgment condition that assesses whether an iteration in the region growing stage stops or not. In some embodiments, the first iteration condition may include that a count of iterative updates reaches a first count threshold, a seed for a next round of iteration cannot be obtained, all pixel points are labeled with region labels, or the like. The first count threshold may be a system default value, a system preset value, or the like.

In some embodiments, the region merging stage 243 includes: performing a plurality of rounds of iterations. At least one round of iterations includes: pairing to-be-merged regions 243-1 in the sweat print image and calculating a second similarity 243-2 between to-be-merged regions in each pair; and merging two to-be-merged regions whose second similarity 243-2 is greater than a second threshold, wherein the to-be-merged region 243-1 is a connected region formed by pixel points with a same region label.

In some embodiments, the pairing may be a random pairing or selecting two regions randomly from adjacent connected regions for pairing. The two adjacent connected regions may be referred to as two to-be-merged regions 243-1 in a pair.

The second similarity 243-2 may be a similarity between the two adjacent connected regions. For example, the second similarity 243-2 may include a similarity of two to-be-merged regions 243-1 for which a pairing is performed.

In some embodiments, the second similarity 243-2 may be determined based on a first similarity between neighboring pixel points of the two to-be-merged regions 243-1. An exemplary manner of calculation is as follows:

$$S = m_1 \times L(A, B) + m_2 \times \frac{1}{N} \sum\nolimits_{a_i \in A, a_i \in B, l(a_i, b_j)=1}^{N} z(a_i, b_j)$$

where L(A, B) denotes a similarity between an average pixel value of a to-be-merged region A and an average pixel value of a to-be-merged region B, $z(a_i, b_j)$ denotes a first similarity between a pixel point $a_i$ and a pixel point $b_j$, $a_i \in A$ denotes that the pixel point $a_i$ is located in the to-be-merged region A, $b_j \in A$ denotes that the pixel point $b_j$ is located in the to-be-merged region B, $l(a_i, b_j)=1$ denotes that the pixel point $a_i$ is neighboring to the pixel point $b_j$, N denotes a count of summation terms, and $m_1$ and $m_2$ denote preset weights.

Manners for calculating the similarity between the average pixel value of the to-be-merged region A and the average pixel value of the to-be-merged region B include but are not limited to, a Euclidean distance, a cosine distance, a Mahalanobis distance, a Chebyshev distance, a Manhattan distance, or the like.

A summation term is a pair of pixel points for calculating the first similarity. In some embodiments, the pair of pixel points may be two pixel points having a neighboring relationship in the two to-be-merged regions 243-1. It should be noted that edges of the two to-be-merged regions 243-1 adjacent to each other may be of various shapes, such as straight lines, stepped lines, or the like. Accordingly, a pixel point may be adjacent to one or more other pixel points.

In some embodiments, the at least one round of iteration includes: for each to-be-merged region 243-1, determining a plurality of target to-be-merged regions capable of being paired with the to-be-merged region 243-1, and for each of the plurality of target to-be-merged regions, determining whether the target to-be-merged region may be merged with the to-be-merged region 243-1. When the second similarity 243-2 between the to-be-merged region 243-1 and the target to-be-merged region is greater than the second threshold, the to-be-merged region 243-1 may be merged with the target to-be-merged region, and the to-be-merged region may be determined as a to-be-merged region for a next round of iteration. A round of iteration is completed when judging whether all target to-be-merged regions of the to-be-merged region are capable of being merged with the to-be-merged region is completed.

In some embodiments, a plurality of to-be-merged regions may be determined based on the to-be-merged region for the next round of iteration. The above steps are repeated to determine whether a merging is capable of being performed until an iteration ends when a second iteration condition is satisfied, and a merged region is obtained.

For different to-be-merged regions, a plurality of merged regions of the sweat print image can be eventually obtained through the plurality of rounds of iteration, realizing the image partitioning of the sweat print image.

The second iteration condition is a judgment condition for assessing whether an iteration in the region merging stage stops or not. In some embodiments, the second iteration condition may include that a count of iterative updates reaches a second count threshold, the to-be-merged region for the next round of iterations cannot be obtained, etc. The second count threshold may be a system default value, a system preset value, or the like.

In some embodiments, the second threshold is related to a difference in pore density of a skin region in which each of the two to-be-merged regions in a pair is located.

More on the pore density can be found in the related description of FIG. 1.

The difference in pore density is a degree of difference in pore density between different skin regions.

The difference in pore density may be obtained in a variety of ways, for example, an absolute value of a difference in pore density of a skin region in which each of the two to-be-merged regions in the pair is located may be determined as the difference in pore density.

In some embodiments, the second threshold is positively correlated with the difference in pore density, and the greater the difference in pore density, the greater the second threshold. The larger the second threshold, the stricter the merging condition for the to-be-merged region.

In some embodiments of the present disclosure, skin regions with different pore densities have different sweating features, and determining the second threshold based on the difference in pore density can make the merging condition for the to-be-merged region more stricter in the case of a greater difference in pore density, which is conducive to improving the accuracy of the image partitioning of the sweat print image, and is conducive to the subsequent calculation of the sweat volume and the sweat rate.

In some embodiments of the present disclosure, connected regions with a same feature can be segmented by the preset division algorithm, so as to provide better boundary information while obtaining a more accurate segmentation result than that based on empirical segmentation.

FIG. 3 is a schematic diagram illustrating an exemplary error prediction model according to some embodiments of the present disclosure.

In some embodiments, a processor may construct an error prediction model 320 based a BP neural network by using a temperature 311, a humidity 312, and a count of regions 313 as an input and a sweat error 330 of a sweat print image as an output.

In some embodiments, the BP neural network (i.e., the error prediction model 320) includes 1 input layer 321, 2 hidden layers 322, and 1 output layer 323. In some embodiments, the input layer 321 includes 3 inputs, each of the hidden layers 322 includes 2 neurons, and the output layer 323 includes 1 output. The hidden layer 322 uses a Sigmoid function as an activation function and the output layer 323 uses a Softmax function as the activation function.

In some embodiments, the hidden layer 322 and the output layer 323 may also use other forms of activation functions, such as a threshold function, a hyperbolic tangent function, or the like.

The input layer 321 is an inputting end of information and is used to read input data. In some embodiments, the BP neural network may include 3 inputs, and may input the temperature 311, the humidity 312, and the count of regions 313 to the input layer 321. A count of neurons in the input layer 311 is the same as a dimension of the input data.

The hidden layer 322 is a processing end of information. The hidden layer 322 passes and fits the input data through the activation function or the like, reduces error for better fitting by back-propagation according to a gradient descent algorithm, and finally passes a processing result to the output layer 323 for a final output.

The output layer 323 is an outputting end of information. In some embodiments, the output layer 323 is used to output the sweat error 330 of the sweat print image. The output layer 323 obtains a same count of neurons as an amount of to-be-fitted data.

In some embodiments of the present disclosure, by constructing the error prediction model based on a BP neural network, and with the help of excellent pattern recognition and classification application features of the BP neural network, mapping of the temperature, humidity, and the count of regions to the sweat error of the sweat print image is realized.

In some embodiments, the error prediction model based on a BP neural network is trained in a manner including following steps S1 to steps S3.

Step S1, initializing a weight parameter and bias parameter of the BP neural network, an initialized weight parameter being a random number between [−1, 1] obeying a normal distribution, and an initialized bias parameter being 0.

Step S2, setting a loss function as:

$$\text{Loss} = \frac{1}{2}\sum(y-y')^2$$

wherein $y$ denotes a real sweat error of a training sample and $y'$ denotes a sweat error predicted by the BP neural network.

Step S3, setting a learning rate and updating the weight parameter and bias parameter of the BP neural network using the gradient descent algorithm to obtain a trained error prediction model.

In some embodiments, the learning rate may be set as 0.01.

In some embodiments, the error prediction model may be trained based on training samples and labels by various ways to update model parameters. For example, the training may be performed based on the gradient descent algorithm. Refer to FIG. 1 and its associated description for more details about the training samples and labels.

In some embodiments, a model training is completed when a loss function of the error prediction model satisfies a preset condition, and the trained error prediction model is obtained. The preset condition may be that the loss function converges, a count of iterations reaches a threshold, etc.

In some embodiments of the present disclosure, setting a plurality of parameters such as the weight parameter, bias parameter, learning rate, and loss function of the BP neural network can make it possible for the error prediction model to reach an optimal value faster during a training process and to obtain a result quickly and accurately.

Figure 4:
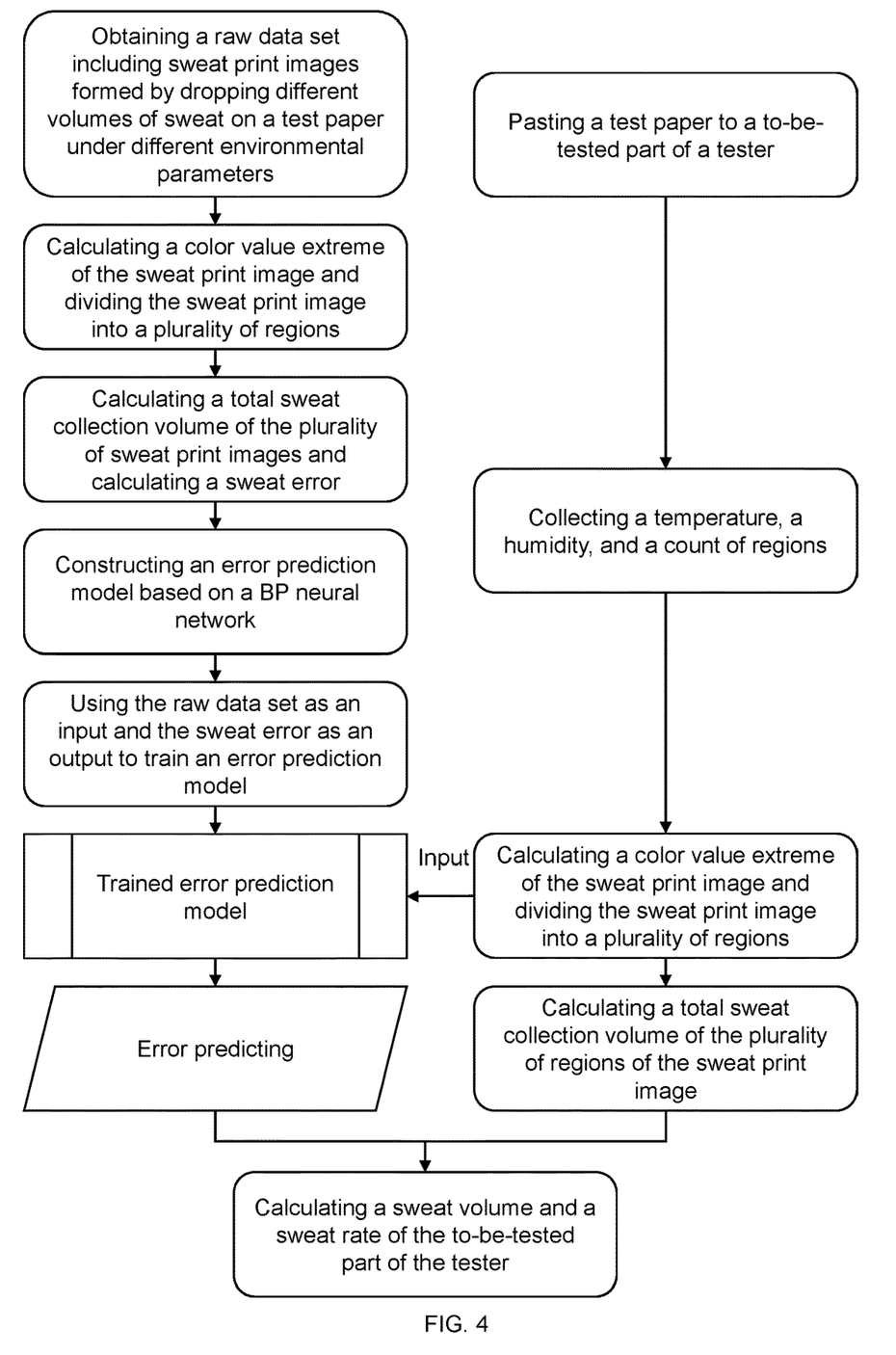
FIG. 4 is a schematic diagram illustrating an exemplary method for sweat detection according to some embodiments.

FIG. 4 is a schematic diagram illustrating an exemplary method for sweat detection according to some embodiments of the present disclosure.

The method for sweat volume detection based on sweat print imaging as shown in FIG. 4 has following steps:
  (1) data collecting: obtaining a raw data set S by collecting sweat print images $X_i$ formed by dropping different volumes of sweat $Q_i$ on a test paper under different temperatures $T_i$ and humidities $H_i$, including:
  (1-1) setting up several sets of experimental environments with a temperature of T and a humidity of H, and dropping different volumes of sweat Q on different test papers in each set of experimental environments;
  (1-2) collecting sweat print images X of each test paper, wherein the test paper shows different colors depending on the different volumes, and the different colors correspond to different color values; and
  (1-3) obtaining the raw data set through steps (1-1) and (1-2) according to a following formula:

$$S=\{s_1(T_1,H_1,Q_1,X_1),s_2(T_2,H_2,Q_2,X_2),\ldots,s_i(T_i,H_i,Q_i,X_i),\ldots,s_n(T_n,H_n,Q_n,X_n)\}$$

where S denotes the raw data set, $s_i$ denotes raw data collected for an i-th time, n denotes a maximum count of sampling times, $T_i$ denotes a temperature collected for the i-th time, $H_i$ denotes a humidity collected for the i-th time, $Q_i$ denotes a real sweat volume collected for the i-th time, and $X_i$ denotes a sweat print image collected for the i-th time.

Merely by way of example, a temperature of 10° C., 15° C., 20° C., 25° C., 30° C., and 35° C. may be set within an airtight chamber, and a humidity may be adjusted to 40% RH, 50% RH, 60% RH, 70% RH under each temperature in turn. Different experiments may be conducted under different conditions of temperature and humidity, respectively. In each experiment, a known volume of sweat is dropped on the test paper through a rubber-tipped burette, and the test paper absorbs a moisture in the sweat and changes color, and the sweat print image is collected by an image collecting device.

(2) image partitioning: identifying a color value of the sweat print image $X_i$ collected in step (1), calculating a color value extreme $\Delta x_i$, and dividing the sweat print image $X_i$ into $m_i$ regions according to the color value extreme $\Delta x_i$, including:
  (2-1) identifying the color value of the sweat print image $X_i$ according to its color, obtaining a maximum extreme value $x_{i_{max}}$ and a minimum extreme value $x_{i_{min}}$ of the color value, and calculating the color value extreme $\Delta x_i$ according to the maximum extreme value $x_{i_{max}}$ and the minimum extreme value $x_{i_{min}}$ according to a following formula:

$$\Delta x_i = x_{i_{max}} - x_{i_{min}}$$

(2-2) dividing the sweat print image $X_i$ into the $m_i$ regions based on the color value extreme $\Delta x_i$:

$$m_i = \begin{cases} m_1 & \Delta x_i < x_1 \\ m_2 & x_1 < \Delta x_i < x_2 \\ m_3 & x_2 < \Delta x_i < x_3 \\ m_4 & x_4 < \Delta x_i \end{cases}$$

where $m_i$ denotes the count of regions, $x_1$, $x_2$, $x_3$, and $x_4$ denote the color value extreme thresholds, and $\Delta x_i$ denotes the color value extreme.

Merely by way of example, a color value of the test paper ranges from 0 to 100. When the color value of the test paper is 100, the color of the test paper is pink. When the color value of the test paper changes from 30 to 99, the color of the test paper changes from light blue to light pink and then to pink. When the color value of the test paper changes from 1 to 29, the color of the test paper changes from blue to light blue. The sweat print image is collected and identified by the image collecting device, the maximum extreme value $x_{i_{max}}$ and minimum extreme value $x_{i_{min}}$ of the color value of the sweat print image are identified, and the color value extreme $\Delta x_i$ is calculated, so as to determine a count of segments of a color value range. In the above example, the $x_1$, $x_2$, $x_3$, and $x_4$ are 10, 30, 60, 90, respectively; $m_1$, $m_2$, $m_3$, and $m_4$ are 2, 4, 12, and 18, respectively, and a segmentation process is an equalization based on the color value range.

(3) error calculating: calculating a total sweat collection volume $Q'_i$ of the $m_i$ regions and calculating a sweat error $\Delta Q_i$ based on the total sweat collection volume $Q'_i$ and a real sweat volume $Q_i$, including:
  (3-1) calculating sweat collection volumes of the $m_i$ regions, respectively and summing the sweat collection volumes to obtain the total sweat collection volume $Q'_i$ according to a following formula:

$$Q'_i = (kx'_1+b)a_1 + (kx'_2+b)a_2 + ,\ldots, (kx'_p+b)a_p, \ldots, +(kx'_m+b)a_m$$

where $x'_p$ denotes a median color value of a p-th region, $a_p$ denotes an area of the p-th region, k and b denote preset coefficients, $(ky'_p+b)a_p$ denotes a sweat collection volume of the p-th region, and m is a count of regions.
  (3-2) calculating the sweat error $\Delta Q_i$ between the total sweat collection volume $Q'_i$ and the real sweat volume $Q_i$ according to a following formula:

$$\Delta Q_i = Q_i - Q'_i$$

In embodiments of the present disclosure, a change in a color value of the test paper varies linearly according to a sweat volume absorbed by the test paper, all of which are preset coefficients of linear variation and are determined by material properties of the test paper.

(4) model constructing: constructing an error prediction model based on a BP neural network using a temperature $T_i$, a humidity $H_i$, and the $m_i$ regions as an input and the sweat error $\Delta Q_i$ as an output.

In some embodiments, the BP neural network includes 1 input layer, 2 hidden layers, and 1 output layer. The input layer includes 3 inputs, each of the hidden layers includes 2 neurons, and the output layer includes 1 output. The hidden layer uses a Sigmoid function as an activation function. The output layer uses a Softmax function as the activation function.

In embodiments of the present disclosure, in a process for sweat detection, the test paper may also be affected by the temperature and humidity when a color change reaction occurs, and there is a difference in the sweat volume between different regions in a process for dropping sweat (simulating the human body's localized differences in the process for dropping sweat, and each region of the test paper has a different degree of fit with the human body). Therefore, using the temperature $T_i$, the humidity $H_i$, and the $m_i$ regions as the input of the BP neural network adequately takes into account the effects of environmental factors and segmentation errors on a sweat detection.

(5) model training: using the temperature $T_i$, the humidity $H_i$, and the $m_i$ regions of the raw data set as the input, training parameters of the error prediction model to obtain a trained error prediction model, including:

(5-1) initializing a weight parameter and a bias parameter of the BP neural network, an initialized weight parameter being a random number between [−1, 1] obeying a normal distribution, and an initialized bias parameter being 0;

(5-2) setting a loss function as follows:

$$\text{Loss} = \frac{1}{2}\sum(y - y')^2$$

where γ denotes a real sweat error of a sample and y' denotes an error predicted by the neural network;

(5-3) setting a learning rate as α and adopting a gradient descent algorithm to update the weight parameter and bias parameter of the BP neural network to obtain the trained error prediction model.

In embodiments of the present disclosure, a learning rate of the gradient descent algorithm is set as 0.01.

(6) sweat volume predicting: pasting a test paper to a to-be-tested part of a tester, collecting environmental parameters and obtaining a to-be-tested sweat print image X' formed on the test paper after a Δt time, dividing the to-be-tested sweat print image X' into m' regions and calculating a total sweat collection volume Q', inputting the environmental parameters and the m' regions into the trained error prediction model obtained in step (5) for calculating the sweat error ΔQ', and calculating a sweat volume and a sweat rate R of the to-be-tested part of the tester, comprising:

(6-1) pasting the test paper to the to-be-tested part of the tester, collecting a temperature T', a humidity H', and the sweat print image X' formed on the test paper after the Δt time.

(6-2) dividing the sweat print image X' into m' regions based on the sweat print image X' according to step (2), and calculating the total sweat collection volume Q' of the m' regions according to step (3);

(6-3) inputting the temperature T', the humidity H', and the m' regions into the trained error prediction model obtained in step (5) to calculate the sweat error ΔQ';

(6-4) summing the total sweat collection volume Q' and a correction error ΔQ' to obtain the sweat volume of the to-be-tested part of the tester, and calculating the sweat rate R of the to-be-tested part of the tester according to a following formula:

$$R = \frac{Q' + \Delta Q'}{a}$$

where α denotes an effective area of the test paper pasted to the to-be-tested part of the tester.

In the embodiment of the present disclosure, by detecting the sweat volume of the tester, it is possible to judge a sweating physique of the tester's body and a strength of a sweating function of the tester. Through the strength of the sweating function of the tester, the sweating physique of the tester's body can be divided into an extremely sweaty body, easy sweaty body, uneasy sweaty body, and extremely unsweaty body, and according to a classification of the body, tester's daily exercise in sports, work intensity, and working hours, and a volume of water to replenish when working or exercising can be provided with guidance.

When describing the operations performed in the embodiments of the present disclosure in terms of steps, the order of the steps is all interchangeable if not otherwise indicated, the steps can be omitted, and other steps can be included in the course of the operation.

The embodiments in the present disclosure are intended to be exemplary and illustrative only and do not limit the scope of application of the present disclosure. Various amendments and changes made under the guidance of the present disclosure remain within the scope of the present disclosure for those skilled in the art. Certain features, structures, or characteristics of one or more embodiments of the present disclosure may be suitably combined.

Aspects of the present disclosure may be performed entirely by hardware, entirely by software (including firmware, resident software, microcode, etc.), or by a combination of hardware and software. All of the above hardware or software can be referred to as "blocks", "modules", "engines", "units", "components" or "systems", and so on. In addition, aspects of the present disclosure may be manifested as a computer product disposed in one or more computer-readable media, and the product includes a computer-readable program code.

A computer storage medium may be any computer-readable medium that can be used to communicate, disseminate, or transmit a program for use by connecting to an instruction-executing system, device, or apparatus. The program code located on the computer storage medium may be propagated through any suitable medium, including radio, cable, fiber optic cable, RF, or the like, or any combination of the foregoing.

The computer program code required for the operation of the various sections of the present disclosure may be written in any one or more programming languages. The program code may be run entirely on the user's computer, or as a stand-alone software package on the user's computer, or partly on the user's computer and partly on a remote computer, or entirely on a remote computer or processing device. In the latter case, the remote computer can be connected to the user's computer through any form of network, such as a local area network (LAN) or wide area network (WAN), or connected to an external computer (e.g., via the Internet), or in a cloud computing environment, or used as a service such as software as a service (SaaS).

It should be noted that in order to simplify the presentation of the disclosure of the present disclosure, and thereby aid in the understanding of one or more embodiments of the present disclosure, the preceding description of embodiments of the present disclosure sometimes combines multiple features into a single embodiment, accompanying drawings, or description thereof. However, this method of disclosure does not imply that the object of the present disclosure requires more features than those mentioned in the claims. Rather, claimed subject matter may lie in less than all features of a single foregoing disclosed embodiment.

The embodiments described in the present disclosure are intended only to illustrate the principles of the embodiments of the present disclosure. Other deformations may also fall within the scope of the present disclosure. Thus, by way of example and not limitation, alternative configurations of embodiments of the present disclosure may be considered consistent with the teachings of the present disclosure. Accordingly, the embodiments of the present disclosure are not limited to the embodiments expressly presented and described herein.

What is claimed is:

1. A method for sweat volume detection based on sweat print imaging, comprising:

data collecting: obtaining a raw data set, the raw data set including at least one sweat print image formed by dropping different volumes of sweat on a test paper under different environmental parameters, the environmental parameters including a temperature and a humidity;

image partitioning: identifying a color value of the at least one sweat print image, obtaining a color value extreme, and dividing the at least one sweat print image into a preset count of first regions according to the color value extreme;

model constructing:

calculating a total sweat collection volume of the at least one sweat print image and calculating a sweat error based on the total sweat collection volume and a real sweat volume, wherein the sweat error is obtained by:

obtaining a sweat collection volume of at least one first region and summing the sweat collection volume of the at least one first region to obtain the total sweat collection volume:

$$Q'_i = (kx'_1+b)a_1 + (kx'_2+b)a_2 + \ldots , (kx'_p + b)a_p, \ldots , +(kx'_m+b)a_m,$$

wherein $x'_p$ denotes a median color value of a p-th region of the at least one sweat print image, $a_p$ denotes an area of the p-th region of the at least one sweat print image, k and b denote preset coefficients, $(ky'_p+b)a_p$ denotes a sweat collection volume of the p-th region of the at least one sweat print image, $Q'_i$ denotes the total sweat collection volume, and m denotes a count of first regions; and determining the sweat error based on a difference between the total sweat collection volume and the real sweat volume; and constructing an error prediction model based on a Back-propagation (BP) neural network using the temperature, the humidity, and the count of first regions as an input of the error prediction model and the sweat error as an output of the error prediction model;

model training using the temperature, the humidity, and the count of first regions of the raw data set as the input of the error prediction model, and training parameters of the error prediction model to obtain a trained error prediction model; and sweat volume predicting:

pasting a test paper to a to-be-tested part of a tester to obtain a to-be-tested sweat print image formed on the pasted test paper after a preset time period;

dividing the to-be-tested sweat print image into at least one region and calculating a total sweat collection volume of the to-be-tested sweat print image;

obtaining current environmental parameters, inputting the current environmental parameters and a count of second regions of the to-be-tested sweat print image into the trained error prediction model, and determining a sweat error of the to-be-tested sweat print image; and calculating a sweat volume and a sweat rate of the to-be-tested part based on the sweat error of the to-be-tested sweat print image.

2. The method of claim 1, wherein the data collecting is implemented by:

setting up at least one set of experimental environmental parameters and dropping different volumes of sweat on different test papers under each set of experimental environmental parameters; and collecting sweat print images of different test papers to obtain the raw data set, wherein the test papers show different colors according to the different volumes, and the different colors correspond to different color values, and the raw data set is as follows:

$$S = \{s_1(T_1,H_1,Q_1,X_1), s_2(T_2,H_2,Q_2,X_2), \ldots , s_i(T_i,H_i,Q_i,X_i), \ldots , s_n(T_n,H_n,Q_n,X_n)\}$$

wherein S denotes the raw data set, $s_i$ denotes raw data collected for an i-th time, n denotes a maximum count of sampling times, $T_i$ denotes a temperature collected for the i-th time, $H_i$ denotes a humidity collected for the i-th time, $Q_i$ denotes a real sweat volume collected for the i-th time, and $X_i$ denotes the at least one sweat print image collected for the i-th time.

3. The method of claim 1, wherein the count of first regions is determined by a following formula:

$$m_i = \begin{cases} m_1 & \Delta x_i < x_1 \\ m_2 & x_1 < \Delta x_i < x_2 \\ m_3 & x_2 < \Delta x_i < x_3 \\ m_4 & x_4 < \Delta x_i \end{cases}$$

wherein $m_i$ denotes the count of first regions, $x_1$, $x_2$, $x_3$, and $x_4$ denote color value extreme thresholds, and $\Delta x_i$ denotes the color value extreme.

4. The method of claim 1, wherein the BP neural network includes one input layer, two hidden layers, and one output layer, wherein the input layer includes three inputs, each of the hidden layers includes two neurons, the output layer includes one output, the hidden layers adopt a Sigmoid function as an activation function, and the output layer adopts a Softmax function as an activation function.

5. The method of claim 1, wherein the model training includes:

initializing a weight parameter and a bias parameter of the BP neural network, an initialized weight parameter being a random number between [−1, 1] obeying a normal distribution, and an initialized bias parameter being 0;

setting a loss function as:

$$Loss = \frac{1}{2}\sum(y-y')^2$$

wherein y denotes a real sweat error of a training sample and y' denotes a sweat error predicted by the BP neural network; and setting a learning rate as α, updating the weight parameter and the bias parameter of the BP neural network using a gradient descent algorithm to obtain the trained error prediction model.

6. The method of claim 1, the calculating the sweat volume and the sweat rate of the to-be-tested part based on the sweat error of the to-be-tested sweat print image includes:

summing the total sweat collection volume of the to-be-tested sweat print image and the sweat error of the to-be-tested sweat print image to obtain the sweat volume of the to-be-tested part and calculating the sweat rate of the to-be-tested part of the tester;

the sweat rate being obtained through a following formula:

$$R = \frac{Q' + \Delta Q'}{a}$$

wherein R denotes the sweat rate, a denotes an effective area of the test paper pasted to the to-be-tested part of the tester, Q' denotes the total sweat collection volume of the to-be-tested sweat print image, and ΔQ' denotes the sweat error of the to-be-tested sweat print image.

7. The method of claim 1, wherein the environmental parameters further include a wind speed and the wind speed is obtained by an airflow sensor.

8. The method of claim 1, wherein the image partitioning is further implemented by:

calculating an image gradient distribution of the at least one sweat print image, the image gradient distribution including an image gradient of each pixel point in the at least one sweat print image; and dividing the at least one sweat print image into the at least one region using a preset division algorithm based on the color value extreme of the at least one sweat print image and the image gradient distribution, wherein the preset division algorithm includes an initialization stage, a region growing stage, and a region merging stage;

wherein the initialization stage includes:
determining a preset count of pixel points in the at least one sweat print image as seeds based on the color value extreme, and assigning a region label for each seed;

the region growing stage includes:
performing a plurality of rounds of iteration, at least one round of iteration including:
determining one or more seeds in a current round of iteration;
for each of the one or more seeds in the current round of iteration, calculating a first similarity between the seed and a neighboring pixel point of the seed, assigning a neighboring pixel point whose first similarity with the seed is greater than a first threshold with a region label corresponding to the seed, and determining the neighboring pixel point as a seed for a next round of iteration; the first similarity being determined based on a similarity of color values between two pixel points and a similarity of image gradients between the two pixel points; and the region merging stage includes:
performing a plurality of rounds of iteration, at least one round of iteration including:
pairing to-be-merged regions in the at least one sweat print image, calculating a second similarity between to-be-merged regions in each pair, the second similarity being determined based on a first similarity between neighboring pixel points of the to-be-merged regions in the pair; and
merging the to-be-merged regions in the pair whose second similarity is greater than a second threshold; wherein the to-be-merged region refers to a connected region formed by pixel points with a same region label.

9. The method of claim 8, wherein the second threshold is related to a difference in pore density of skin regions in which the to-be-merged regions in the pair are located.

10. The method of claim 1, wherein each region corresponds to a set of preset coefficients, the preset coefficients of each region are determined based on a color value distribution feature of each region, and the color value distribution feature includes at least a color value histogram distribution and a color value dispersion degree of each pixel point within each region.

11. The method of claim 10, wherein the preset coefficients of each region are further related to a pore density of a skin region in which each region is located.

\* \* \* \* \*